(12) United States Patent
Belongia

(10) Patent No.: US 9,770,524 B2
(45) Date of Patent: Sep. 26, 2017

(54) VOLATILE MATERIAL DISPENSER AND METHOD OF ATTACHING A REFILL OR REFILLS TO SAME

(75) Inventor: David C. Belongia, Burlington, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 1558 days.

(21) Appl. No.: 12/837,948

(22) Filed: Jul. 16, 2010

(65) Prior Publication Data

US 2012/0012668 A1    Jan. 19, 2012

(51) Int. Cl.
*A61L 9/12*    (2006.01)
*A01M 1/20*    (2006.01)
*A61L 9/03*    (2006.01)

(52) U.S. Cl.
CPC ............ *A61L 9/12* (2013.01); *A01M 1/2072* (2013.01); *A01M 1/2077* (2013.01); *Y10T 29/49817* (2015.01); *Y10T 29/49826* (2015.01)

(58) Field of Classification Search
CPC ... A61L 9/02; A61L 9/03; A61L 9/037; A61L 9/04; A61L 9/12; A61L 9/127; Y10T 29/49817; Y10T 29/49826; A01M 1/2072; A01M 1/2077; A01M 1/2061; A01M 1/2022
USPC .................................. 239/33, 44, 47, 49, 50
See application file for complete search history.

(56) References Cited

U.S. PATENT DOCUMENTS

| | | |
|---|---|---|
| 5,038,394 A | 8/1991 | Hasegawa et al. |
| 5,222,186 A | 6/1993 | Schimanski et al. |
| 5,779,101 A | 7/1998 | Holmgren et al. |
| 6,236,807 B1 | 5/2001 | Ruffolo et al. |
| 6,278,840 B1 | 8/2001 | Basaganas Millan |
| 6,466,739 B2 | 10/2002 | Ambrosi et al. |
| 6,569,387 B1 | 5/2003 | Furner et al. |
| 6,603,924 B2 | 8/2003 | Brown et al. |
| 6,697,571 B2 | 2/2004 | Triplett et al. |
| 6,722,532 B2 | 4/2004 | Lasserre et al. |
| 6,783,117 B2 | 8/2004 | Wohrle |

(Continued)

FOREIGN PATENT DOCUMENTS

| | | |
|---|---|---|
| DE | 4433954 | 3/1996 |
| EP | 0451331 | 10/1991 |

(Continued)

OTHER PUBLICATIONS

PCT/US2011/001252 International Search Report dated Oct. 31, 2011.

*Primary Examiner* — Christopher Kim

(57) ABSTRACT

A method of attaching a refill to a volatile material dispenser includes the step of providing a volatile material dispenser that includes a housing, a first implement that attaches a refill containing a volatile material to the housing, and a second implement that attaches the refill to the housing, wherein the first and second implements include different features. The method further includes the step of attaching the refill in a first orientation to the volatile material dispenser, wherein in the first orientation, the first implement retains the refill. Still further, the method includes the step of attaching the refill in a second orientation different than the first orientation to the volatile material dispenser, wherein in the second orientation, the second implement retains the refill.

5 Claims, 13 Drawing Sheets

(56) References Cited

U.S. PATENT DOCUMENTS

| | | | |
|---|---|---|---|
| 6,859,615 B2 | 2/2005 | Yip et al. | |
| 6,862,403 B2 | 3/2005 | Pedrotti et al. | |
| 6,889,003 B2 | 5/2005 | Triplett et al. | |
| 6,917,754 B2 | 7/2005 | Pedrotti et al. | |
| 6,931,202 B2 | 8/2005 | Pedrotti et al. | |
| 7,324,744 B2 | 1/2008 | Triplett et al. | |
| 7,341,698 B2 * | 3/2008 | Pedrotti | A01M 1/2072 239/34 |
| 7,344,123 B2 | 3/2008 | Pankhurst et al. | |
| 7,389,943 B2 | 6/2008 | Jaworski | |
| 7,400,822 B2 | 7/2008 | Ruiz Ballesteros et al. | |
| D584,809 S | 1/2009 | Porchia et al. | |
| 7,497,354 B2 | 3/2009 | Decottignies et al. | |
| 7,544,332 B2 | 6/2009 | De Silva et al. | |
| 7,722,807 B2 * | 5/2010 | Keller et al. | 422/5 |
| 2002/0172512 A1 | 11/2002 | Stathakis et al. | |
| 2003/0189022 A1 | 10/2003 | Fellows et al. | |
| 2004/0182949 A1 | 9/2004 | Duston et al. | |
| 2004/0247301 A1 | 12/2004 | Yip et al. | |
| 2006/0043619 A1 | 3/2006 | Brown et al. | |
| 2006/0110144 A1 | 5/2006 | Fellows et al. | |
| 2006/0249593 A1 | 11/2006 | Brown et al. | |
| 2007/0048173 A1 * | 3/2007 | Keller et al. | 422/5 |
| 2008/0011874 A1 | 1/2008 | Munagavalasa et al. | |
| 2008/0279731 A1 | 11/2008 | Goreham et al. | |
| 2009/0212124 A1 | 8/2009 | Kenny | |
| 2009/0218413 A1 | 9/2009 | Withers | |
| 2010/0061896 A1 | 3/2010 | Sassoon | |
| 2010/0102088 A1 | 4/2010 | Keller | |

FOREIGN PATENT DOCUMENTS

| | | |
|---|---|---|
| ES | 278519 | 3/1984 |
| GB | 1513953 | 6/1978 |
| GB | 2449703 | 3/2008 |
| WO | 0076292 | 12/2000 |

* cited by examiner

VOLATILE MATERIAL DISPENSER AND METHOD OF ATTACHING A REFILL OR REFILLS TO SAME

CROSS REFERENCE TO RELATED APPLICATIONS

Not applicable.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to volatile material dispensers and, more particularly, to volatile material dispensers having one or more retention features for coupling a refill thereto.

2. Description of the Background of the Invention

Multiple different volatile material dispensers are commercially sold and generally include a housing and a volatile material refill that is inserted into the housing. The refill generally includes a container or bottle for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill can typically be removed by a user and replaced with a new refill.

One type of commercial volatile material dispenser, referred to herein as a plug-in scented oil dispenser, includes a housing and a heater disposed within the housing. A refill for use with a plug-in scented oil dispenser generally includes a container portion having a bottom end and a top end, wherein the container portion terminates in a neck portion at the top end. A volatile material is disposed within the container portion and a wick is in contact with the volatile material and extends out of the refill through the neck portion. A plug or other connector generally positions and retains the wick within the neck portion. Upon insertion of the refill into the dispenser, at least a portion of the wick is disposed adjacent the heater such that volatile material that moves through the wick is volatilized by the heater.

Another feature of various volatile material dispensers and refills is that each refill has features that are unique or complementary to the particular dimensions of the housing of the dispenser for which it is sold. Still further, each refill has a feature that interacts with a further feature in the dispenser for which it is manufactured to retain the refill within the dispenser.

SUMMARY OF THE INVENTION

According to one embodiment, a method of attaching a refill to a volatile material dispenser includes the step of providing a volatile material dispenser that includes a housing, a first implement that attaches a refill containing a volatile material to the housing, and a second implement that attaches the refill to the housing, wherein the first and second implements include different features. The method further includes the step of attaching the refill in a first orientation to the volatile material dispenser, wherein in the first orientation, the first implement retains the refill. Still further, the method includes the step of attaching the refill in a second orientation different than the first orientation to the volatile material dispenser, wherein in the second orientation, the second implement retains the refill.

According to another embodiment, a volatile material dispenser includes a housing, a first implement that secures a refill having a volatile material therein to the housing, and a second implement that secures the refill to the housing, wherein the second implement is different than the first implement. The first implement is capable of retaining the refill when the refill is disposed in a first orientation and the second implement is capable of retaining the refill when the refill is disposed in a second, different orientation.

According to yet another embodiment, a method of attaching two or more refills to a volatile material dispenser includes the step of providing a volatile material dispenser that includes a housing and at least one implement that attaches a refill containing a volatile material to the housing. The method further includes the steps of attaching a first refill to the volatile material dispenser in a first orientation, wherein in the first orientation, at least the implement retains the refill and attaching the first refill to the volatile material dispenser in a second orientation, wherein in the second orientation, at least the implement retains the refill and wherein the first and second orientations are different. The method still further includes the step of attaching a second refill having features different than the first refill to the volatile material dispenser in a third orientation, wherein in the third orientation, at least the implement retains the refill. Additionally, the method includes the step of attaching a second refill to the volatile material dispenser in a fourth orientation, wherein in the fourth orientation, at least the implement retains the refill and wherein the third and fourth orientations are different.

Other aspects and advantages of the present invention will become apparent upon consideration of the following detailed description, wherein similar structures have like or similar reference numerals.

DETAILED DESCRIPTION

The present invention is directed to volatile material dispensers for vaporizing and dispensing volatile materials. While the present invention may be embodied in many different forms, several specific embodiments are discussed herein with the understanding that the present invention is to be considered only as an exemplification of the principles of the invention, and it is not intended to limit the invention to the embodiments illustrated.

Further, the use of the term volatile material herein refers to any volatile material that a consumer may desire to emit into an area surrounding one or more refills holding the volatile material(s) and/or a dispenser holding one or more refills. Illustratively, the types of volatile materials may be, for example, a cleaner, an insecticide, an insect repellant, an insect attractant, a mold or mildew inhibitor, a fragrance, a disinfectant, an air purifier, an aromatherapy scent, an antiseptic, a positive fragrancing volatile material, an air-freshener, a deodorizer, or the like, and combinations thereof. Additives may be included in the volatile material, such as, for example, fragrances and/or preservatives.

Figure 1:
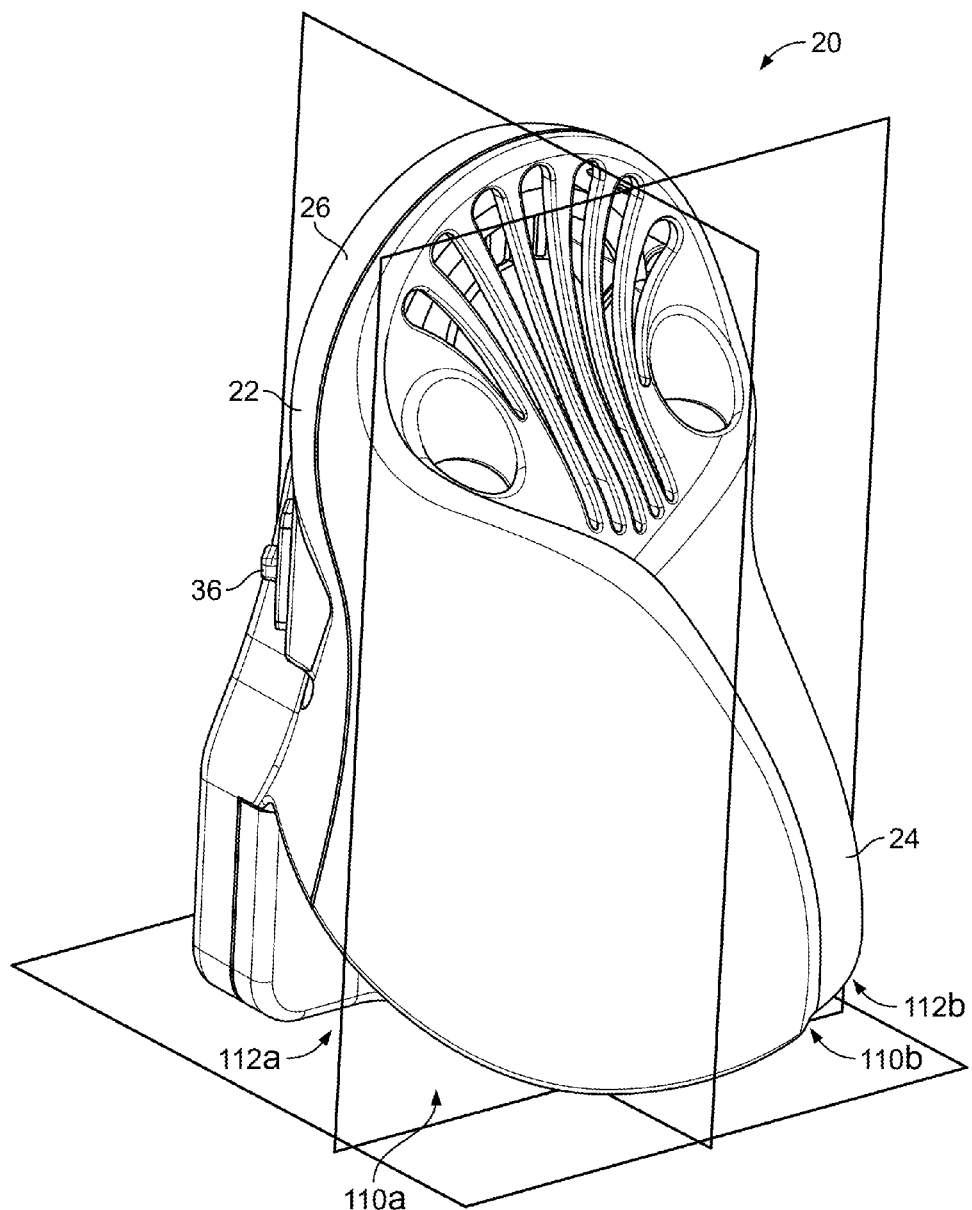
FIG. 1 is a top isometric view of a first embodiment of a volatile material dispenser according to the present invention.
Figure 2:
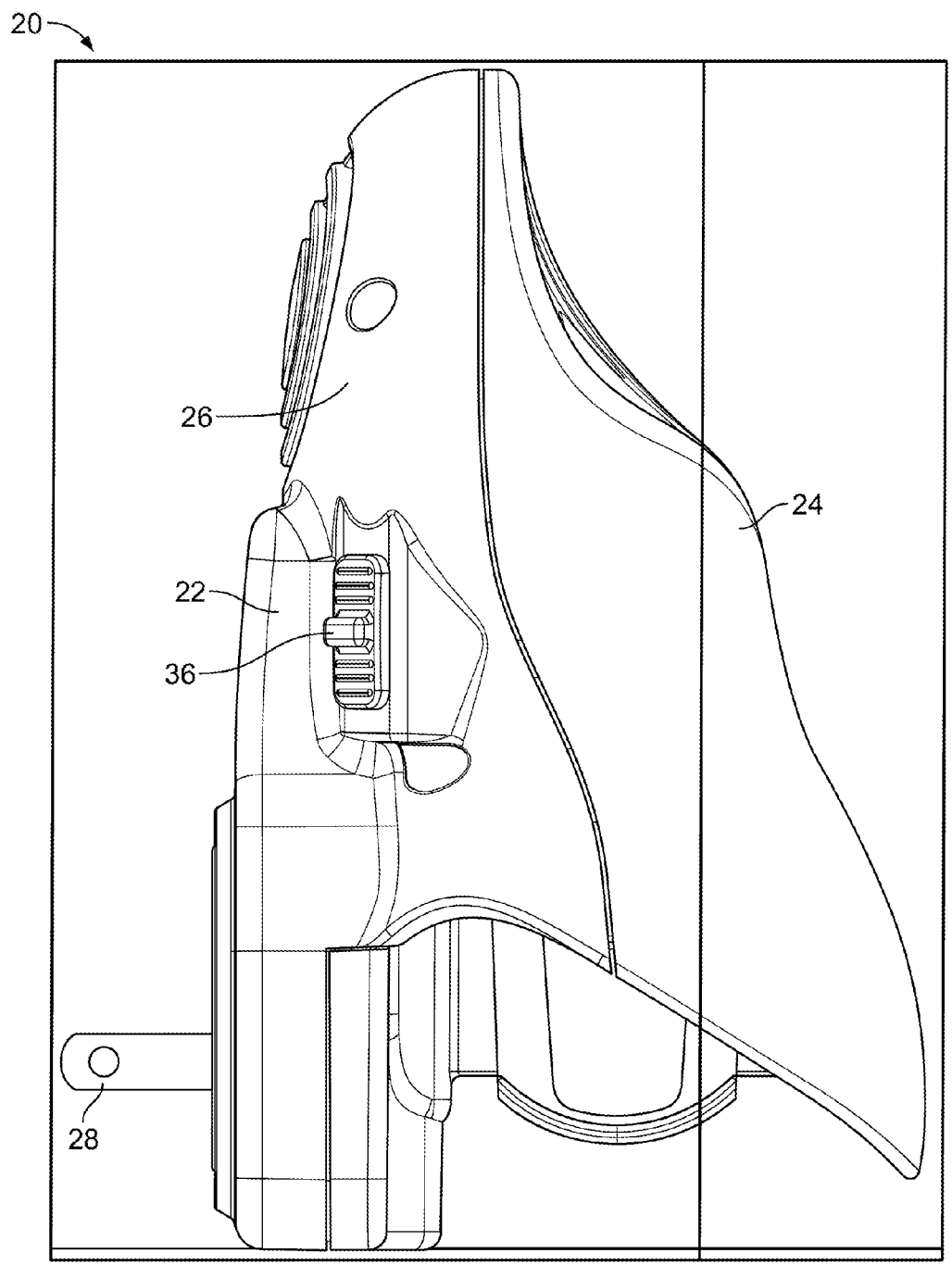
FIG. 2 is a side elevational view of the volatile material dispenser of FIG. 1.

Referring now to FIGS. 1-7, a first embodiment of a volatile material dispenser 20 of the present invention includes a housing 22 formed from a front cover 24 and a rear cover 26. A chassis 28 (FIGS. 3 and 4) is disposed within the housing 22 between the front and rear covers 24, 26 and supports various components, such as, a plug assembly 28 (FIGS. 2, 5, and 6), a printed circuit board (not shown), a fan 30 (FIGS. 3 and 4), first and second ceramic heating bodies 32a, 32b (FIGS. 3 and 4), first and second light emitting diodes (LEDs) 34a, 34b (only 34a shown FIGS. 3 and 4), and a selector switch 36 (FIGS. 1 and 2).

Figure 3:
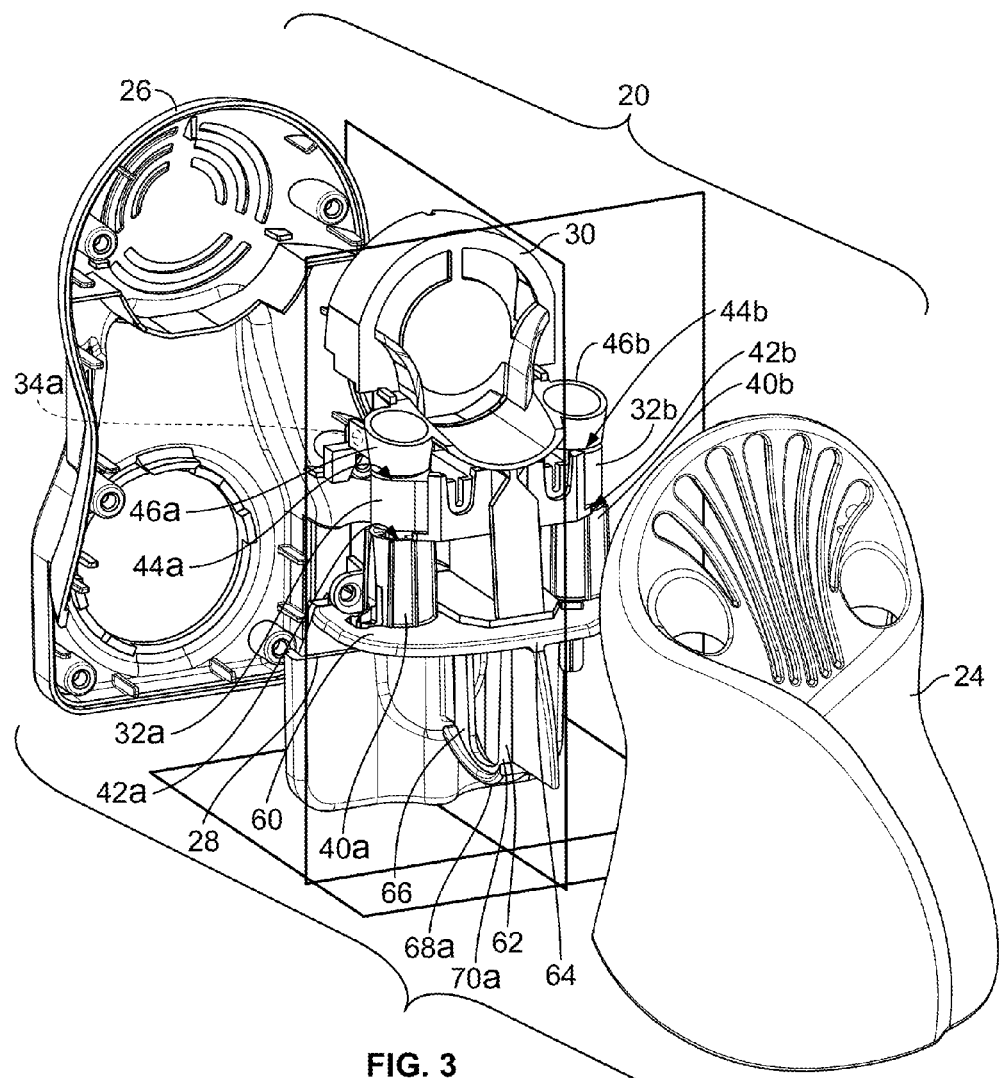
FIG. 3 is an exploded view of the volatile material dispenser of FIG. 1.
Figure 4:
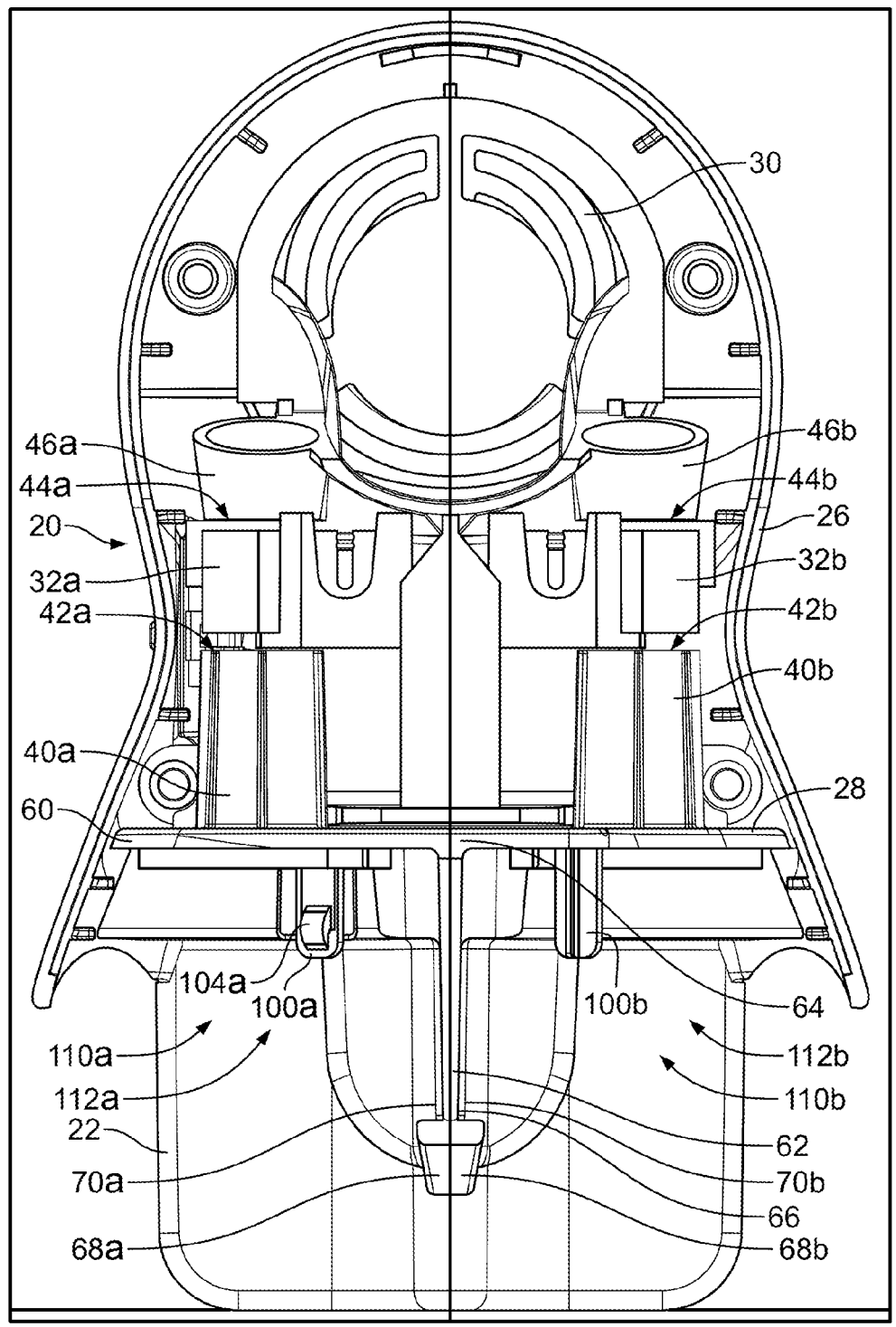
FIG. 4 is a front elevational view of the volatile material dispenser of FIG. 1 with a front cover removed therefrom.

Referring to FIGS. 3 and 4, the chassis 28 generally includes first and second generally cylindrical structures 40a, 40b forming first and second channels 42a, 42b, respectively, wherein the first and second ceramic heating bodies 32a, 32b are disposed above the first and second generally cylindrical structures 40a, 40b, respectively. The heating bodies 32a, 32b further include channels 44a, 44b formed therethrough to accommodate wicks, wherein the channels 44a, 44b are aligned with the channels 42a, 42b through the cylindrical structures 40a, 40b to accommodate wicks. The chassis 28 further includes first and second chimneys 46a, 46b that are disposed above and aligned with the first and second heating bodies 32a, 32b, respectively. The PCB is disposed within the chassis 28 behind the heating bodies 32a, 32b, cylindrical structures 40a, 40b, and the chimneys 46a, 46b, wherein the first and second LEDs 34a, 34b extend from the PCB to points adjacent rear surfaces of the first and second chimneys 46a, 46b, respectively, to illuminate same.

As seen in FIGS. 2-7, the chassis 28 further includes a generally horizontal member 60 disposed at lower ends of the cylindrical structures 40a, 40b and a generally vertical member 62 that is perpendicular to and extends downwardly from a central portion 64 of the horizontal member 60. A lower end 66 of the vertical member 62 is curved and includes curved ledges 68a, 68b extending from opposing sides 70a, 70b thereof and being generally perpendicular to the vertical member 62.

Figure 5:
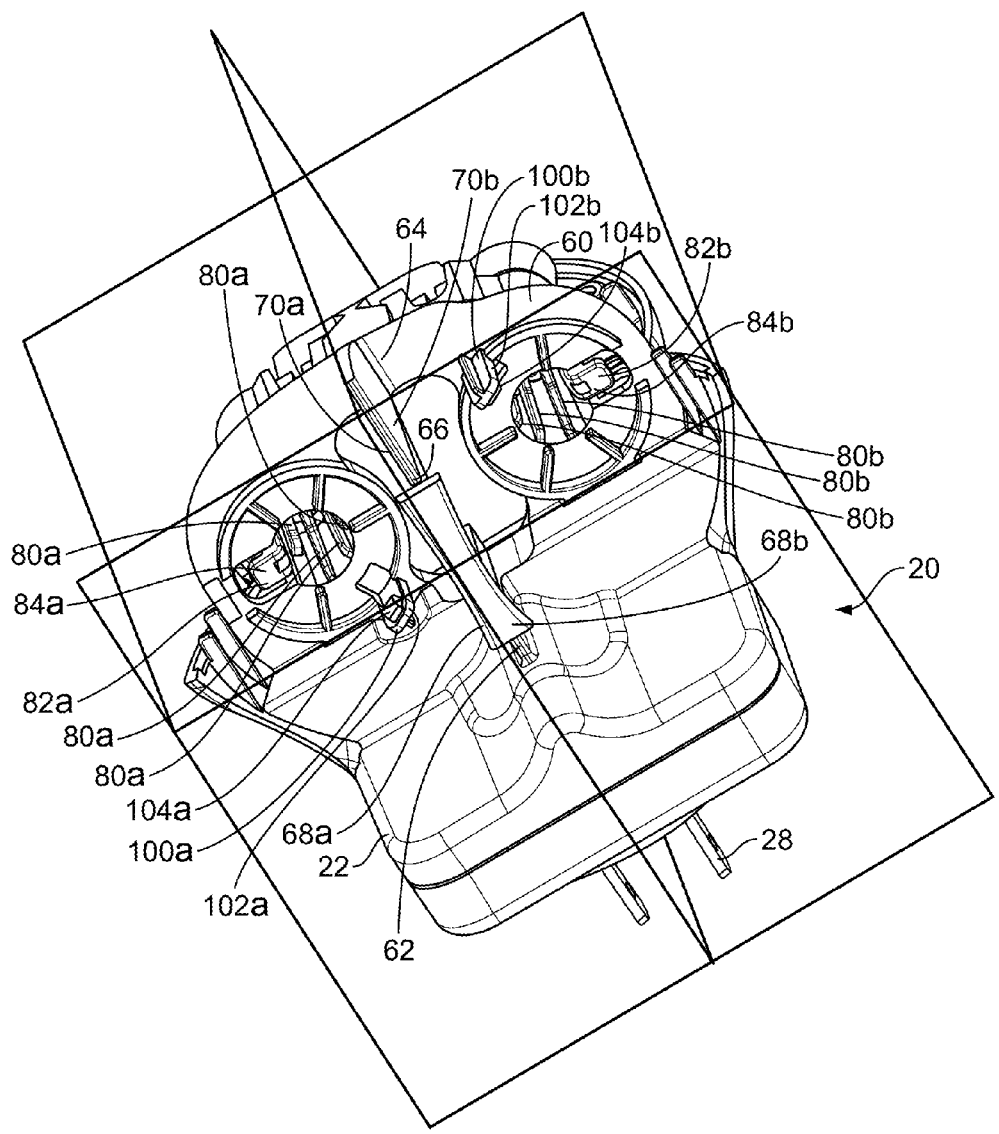
FIG. 5 is a bottom isometric view of the volatile material dispenser of FIG. 1 with the front cover removed therefrom.
Figure 6:
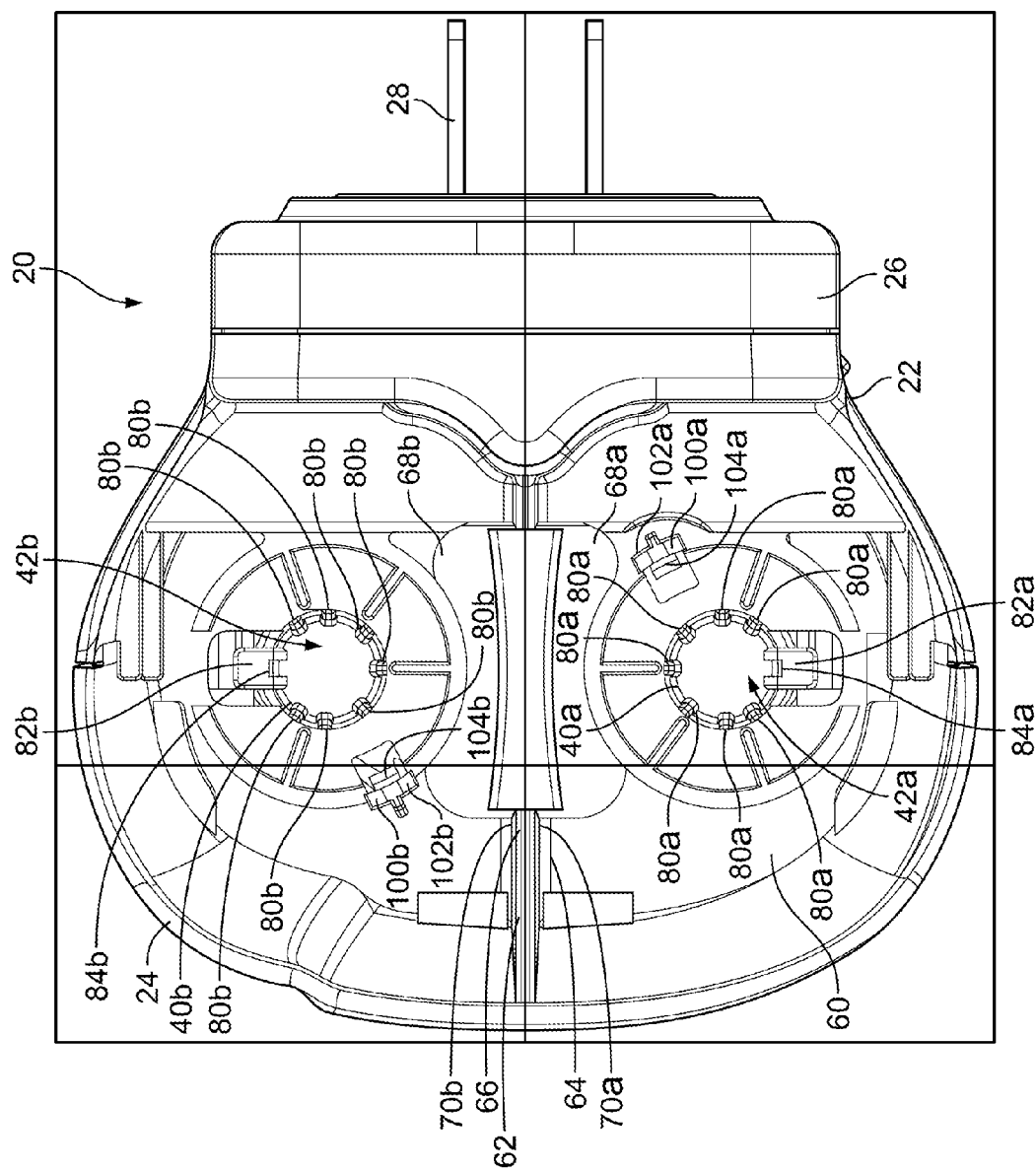
FIG. 6 is a bottom elevational view of the volatile material dispenser of FIG. 1.

The volatile material dispenser 20 includes a number of retention features or implements that aid in retaining a refill therein in more than one orientation, wherein such retention features will be discussed in greater detail hereinafter. Specifically, as seen in FIGS. 5 and 6, the dispenser 20 includes a first retention feature including a plurality of stationary ribs 80a, 80b disposed on inner surfaces along a height (parallel to a vertical axis of the dispenser) of each of the cylindrical structures 40a, 40b and extending into the channels 42a, 42b formed by the cylindrical structures 40a, 40b. Although seven ribs are depicted on each cylindrical structure 40a, 40b, any number of ribs may be utilized. A second retention features includes flexible, movable ribs 82a, 82b forming a part of the cylindrical structures 40a, 40b and extending into the channels 42a, 42b formed by the cylindrical structures 40a, 40b. The movable ribs 82a, 82b are connected to the cylindrical structures 40a, 40b by a hinge or other flexible structure that allows lower ends 84a, 84b of the ribs 82a, 82b to move in and out of the respective channels 42a, 42b. Although only a single movable rib 82a, 82b is depicted in each cylindrical structure 40a, 40b, any number of movable ribs 82a, 82b may be utilized. The function of the ribs 80a, 80b, 82b, 82b will be discussed in greater detail hereinafter.

Still referring to FIGS. 5 and 6, a third retention feature includes first and second latches 100a, 100b extending downwardly from the horizontal member 60 and spaced from the respective cylindrical structures 40a, 40b. Each of the latches 100a, 100b includes a downwardly extending member 102a, 102b and an inwardly extending projection 104a, 104b. The curved ledges 68a, 68b described above provide a fourth retention feature. The function of the ledges 68a, 68b and the latches 100a, 100b will be discussed in greater detail hereinafter.

The first channel 42a, the vertical member 62, the ledge 68a, the stationary ribs 80a, the movable ribs 82a, and the latch 100a are formed within a first cavity 110a of the dispenser 20 and provide a first retention housing 112a for the retention of a first refill. Likewise, the second channel 42b, the vertical member 62, the ledge 68b, the stationary ribs 80b, the movable ribs 82b, and the latch 100b are formed within a second cavity 110b of the dispenser 20 and provide a second retention housing 112b for the retention of a second refill.

Figure 7:
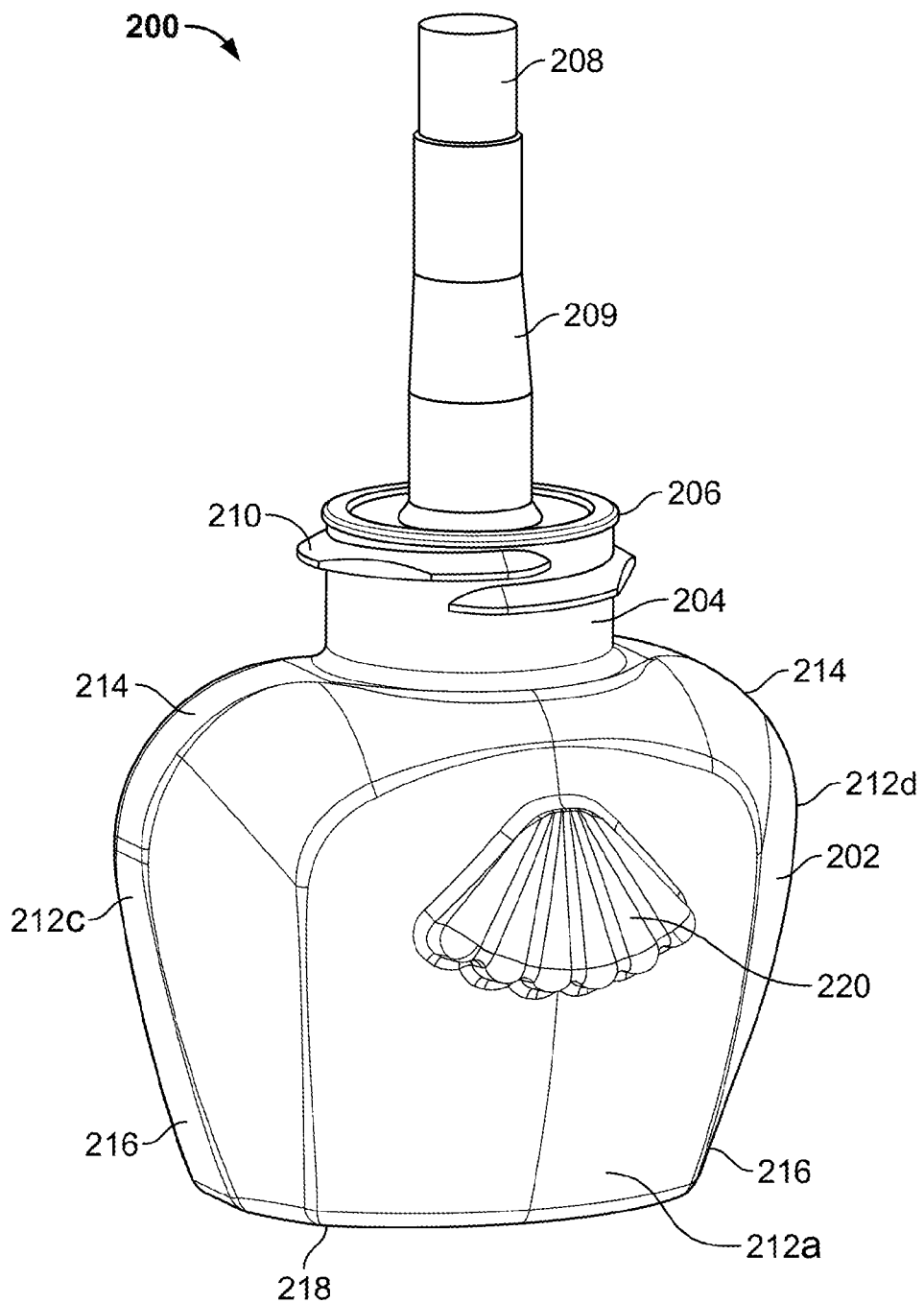
FIG. 7 is a top isometric view of a refill that may be inserted into the volatile material dispensers disclosed herein.
Figure 8:
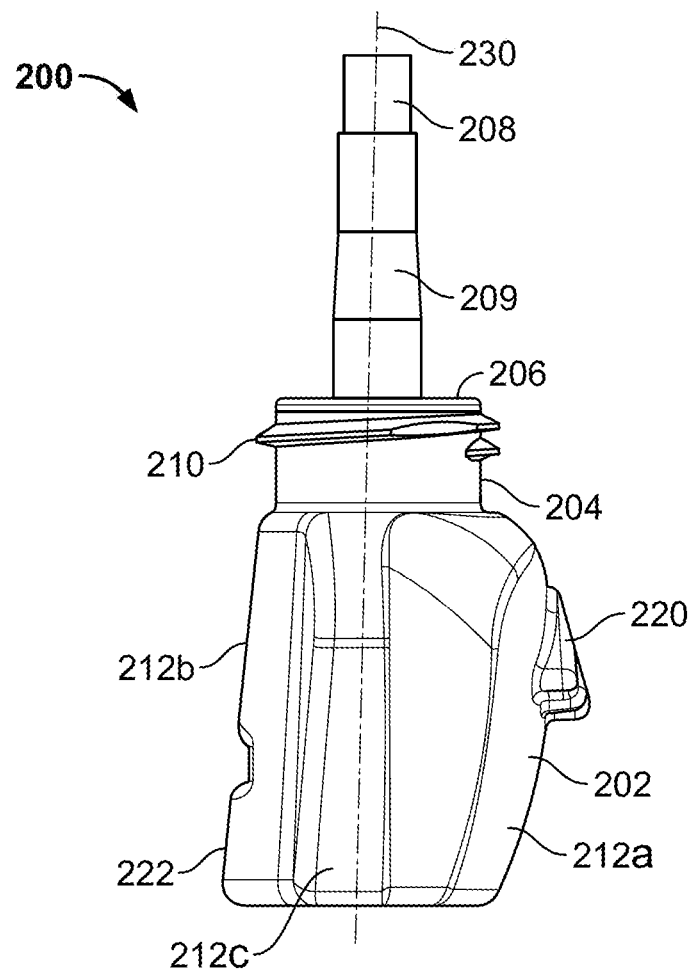
FIG. 8 is a side elevational view of the refill of FIG. 7.
Figure 9:
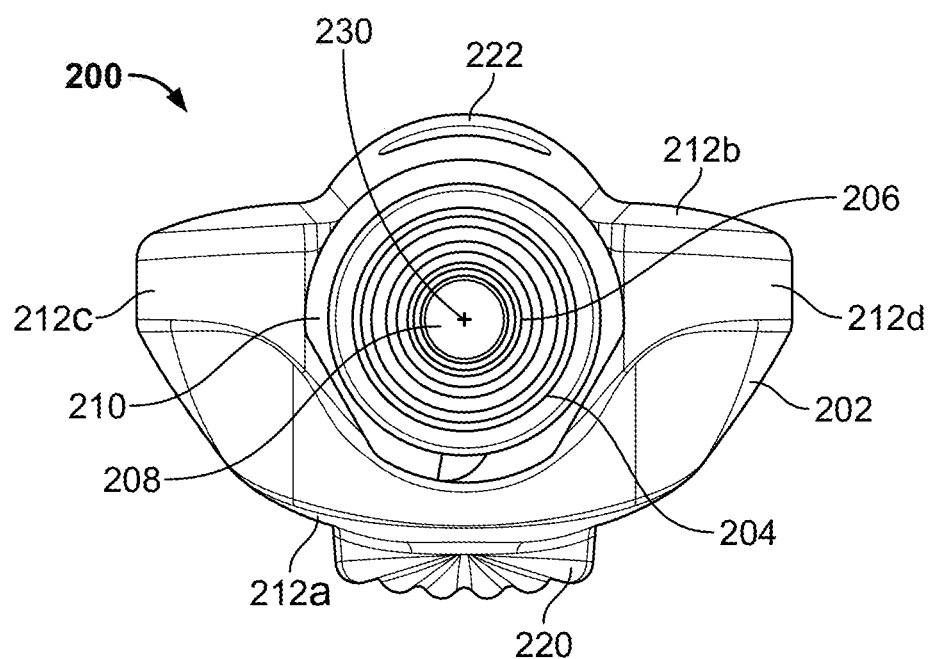
FIG. 9 is a top elevational view of the refill of FIG. 7.

A first refill 200 capable of insertion into the volatile material dispenser 20 is depicted in FIGS. 7-9. The refill 200 generally includes a container portion 202 that holds a volatile material, wherein a cylindrical neck portion 204 extends upwardly from the container portion 202. A plug assembly 206 is disposed within and attached to the neck portion 204 of the refill 200. A wick 208 is disposed in contact with the volatile material inside the container portion 202 and extends upwardly through the neck portion 204, such that a portion of the wick 208 is exposed to a surrounding environment. The wick 208 is retained within the neck portion 204 by the plug assembly 206, wherein a sheath 209 extends upwardly from the plug assembly 206 to surround a portion of the wick 208. A thread 210 is disposed on the neck portion 204, wherein the thread 210 may retain a cap (not shown) thereon and/or may aid in retaining the refill 200 within the dispenser 200, as discussed in greater detail hereinafter.

The container portion 202 of the refill 200 includes front and rear surfaces 212a, 212b and first and second side surfaces 212c, 212d connecting the front and rear surfaces 212a, 212b. The front surface 212a has a generally bulbous central portion and is generally curved inwardly at sides and a bottom thereof and the rear surface 212b is generally planar. Further, and referring to FIG. 7, the side surfaces 212c, 212d begin at the neck portion 204 and curve outwardly at top portions 214 thereof and inwardly at bottom portions 216 thereof to generally form a heart shape that is truncated at a bottom surface 218 thereof. A shell-shaped protrusion 220 extends outwardly from the front surface 212a and a semi-cylindrical projection 222 extends outwardly from the rear surface 212b along a height of the container portion 202.

Figure 10:
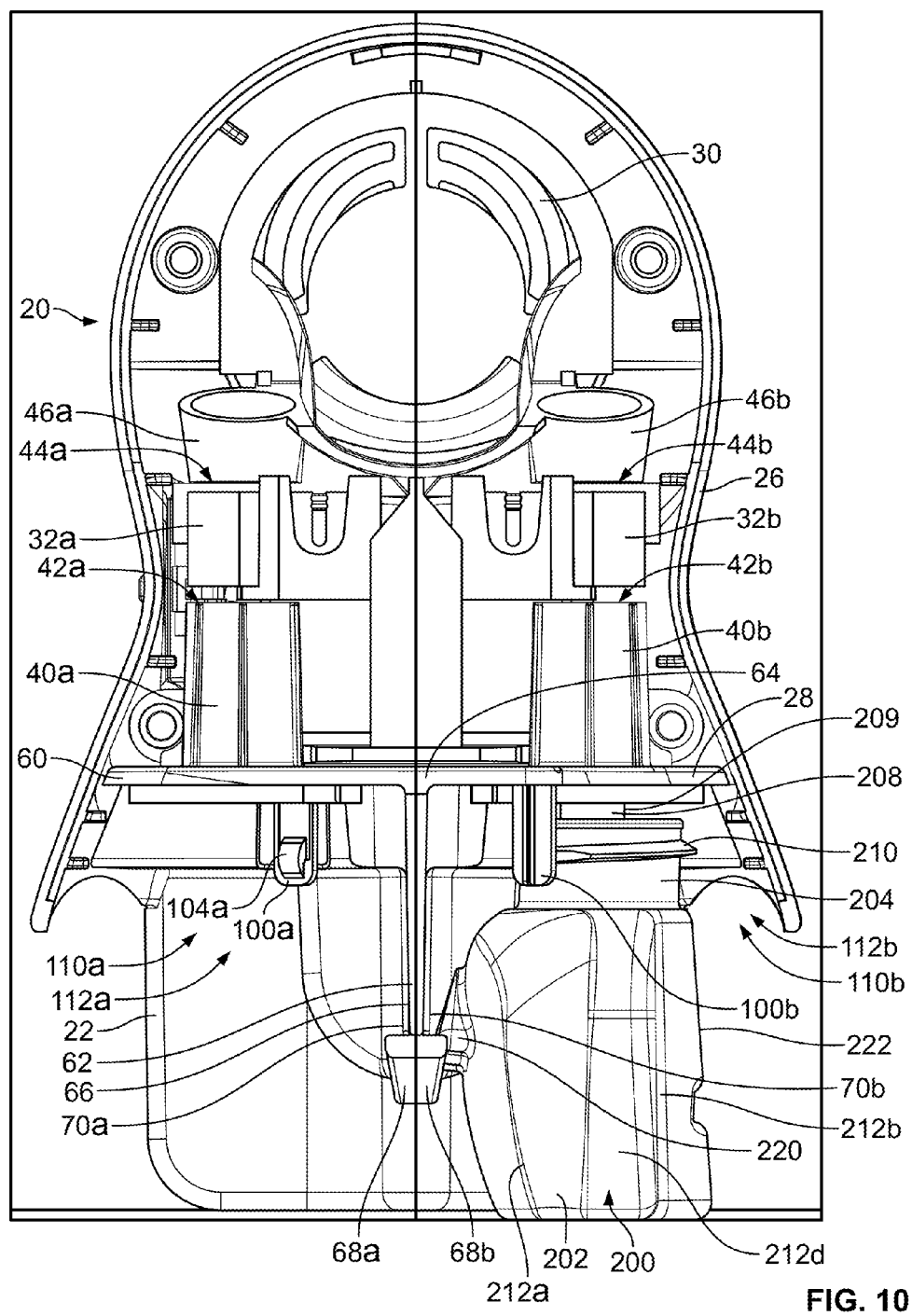
FIG. 10 is a front elevational view of the volatile material dispenser of FIG. 4 with the refill of FIGS. 7-9 inserted therein in a first orientation.
Figure 11:
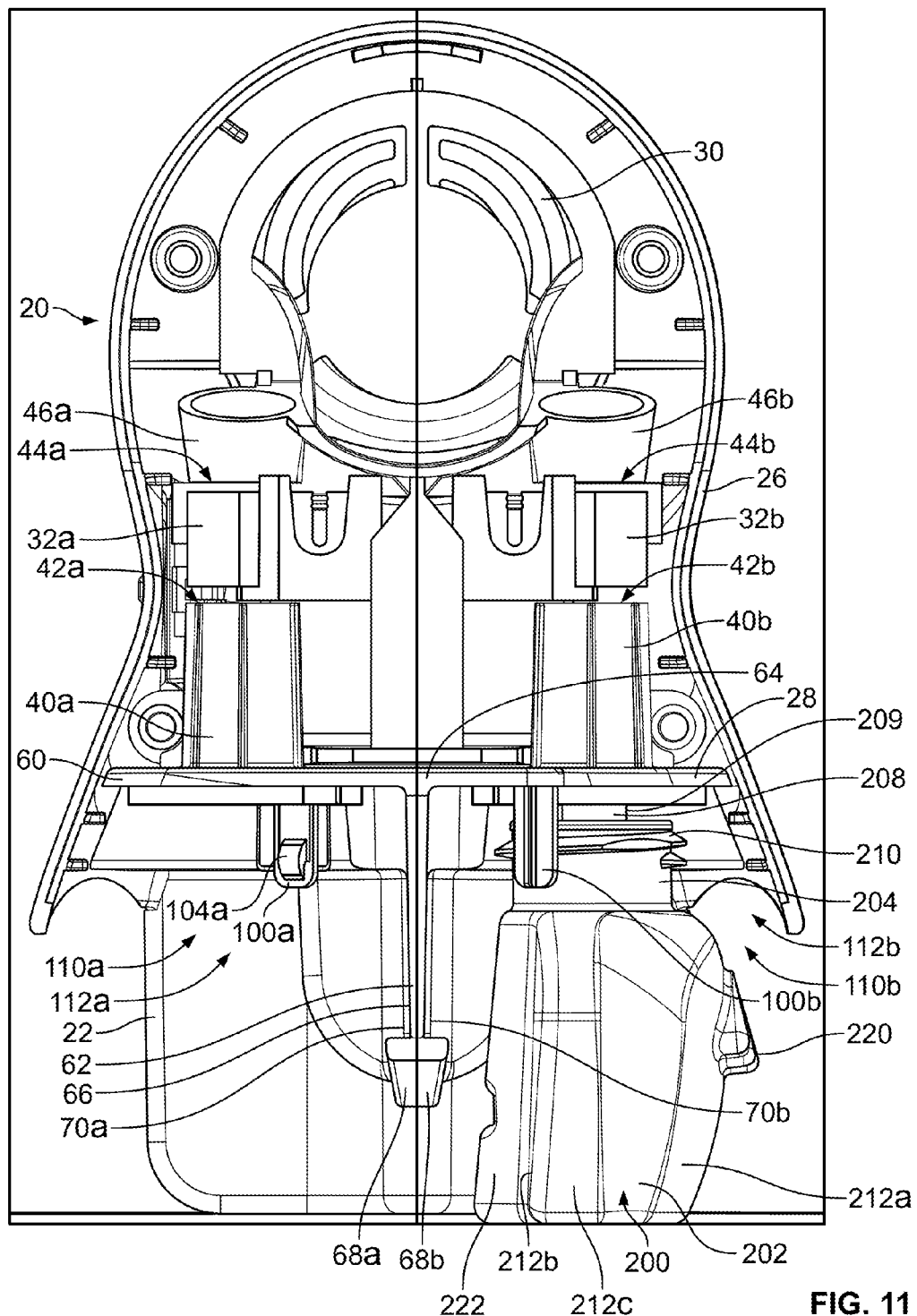
FIG. 11 is a front elevational view of the volatile material dispenser of FIG. 4 with the refill of FIGS. 7-9 inserted therein in a second orientation.

FIGS. 10 and 11 depict the refill 200 inserted into and retained within the second retention housing 112b of the dispenser 20 in first and second orientations, respectively. In the first orientation of FIG. 10, the wick 208 and sheath 209 are inserted into the channel 42a and the refill 200 is pushed upwardly until the latch 100b meets the thread 210 on the refill 200. As the thread 210 passes the latch 100b, an interference between the thread 210 and the projection 104b on the latch 100b causes the latch 100b to flex outwardly until the thread 210 passes the projection 104b. During such movement, the stationary ribs 80b create an interference fit between the sheath 209 surrounding the wick 208 of the refill 200. The movable rib 82b allows for a bit of give or movement of the wick 208 and sheath 209 such that the interference fit is not too tight. The stationary ribs 80b and movable rib 82b create a horizontal load on the sheath 209 that aids in retaining the wick 208 within the channel 42a. Once the thread 210 passes the projection 104b, the refill 200 is in a retained position, wherein the stationary and movable ribs 80b, 82b partially retain the wick 208 and the sheath 209 in place, the projection 104b extending from the latch 100b interferes with the thread 210 to prevent downward movement of the refill 200, and the protrusion 220 extending from the refill 200 sits on the ledge 68b to also prevent downwardly movement of the refill 200.

In the second orientation of FIG. 11, the refill 200 has been rotated 180 degrees about a vertical axis 230 (FIGS. 8 and 9) of the refill 200. In such orientation, the wick 208 and sheath 209 are inserted and retained in the same manner as with the first orientation (by the stationary and movable ribs 80b, 82b). Additionally, the projection 104b extending from the latch 100b provides an interference with the thread 210 to prevent downward movement of the refill 200. In this orientation, the refill 200 is not retained in any way by the protrusion 220 extending therefrom.

Although a thread 210 is utilized to interact with the latch 100b, any annular member, projection, or other structure that interacts with the latch 100b to prevent downward movement may alternatively be utilized. Still alternatively, the thread 210 may be discontinuous.

Although the refill 200 is shown inserted into and retained within the second retention housing 112b, the refill 200 can be retained in first and second orientations within the first retention housing 112a. In particular, in the first orientation, the protrusion 220 extending from the refill 200 is captured by the ledge 68a and in the second orientation, the protrusion 220 extends outwardly away from the ledge 68a and is not utilized to retain the refill 200 within the dispenser 20.

Figure 12:
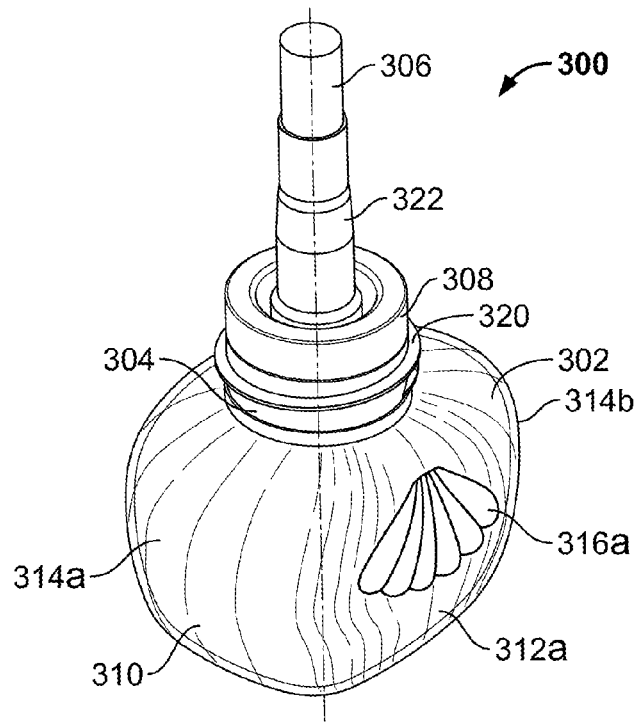
FIG. 12 is a top isometric view of another refill that may be inserted into the volatile material dispensers disclosed herein.
Figure 13:
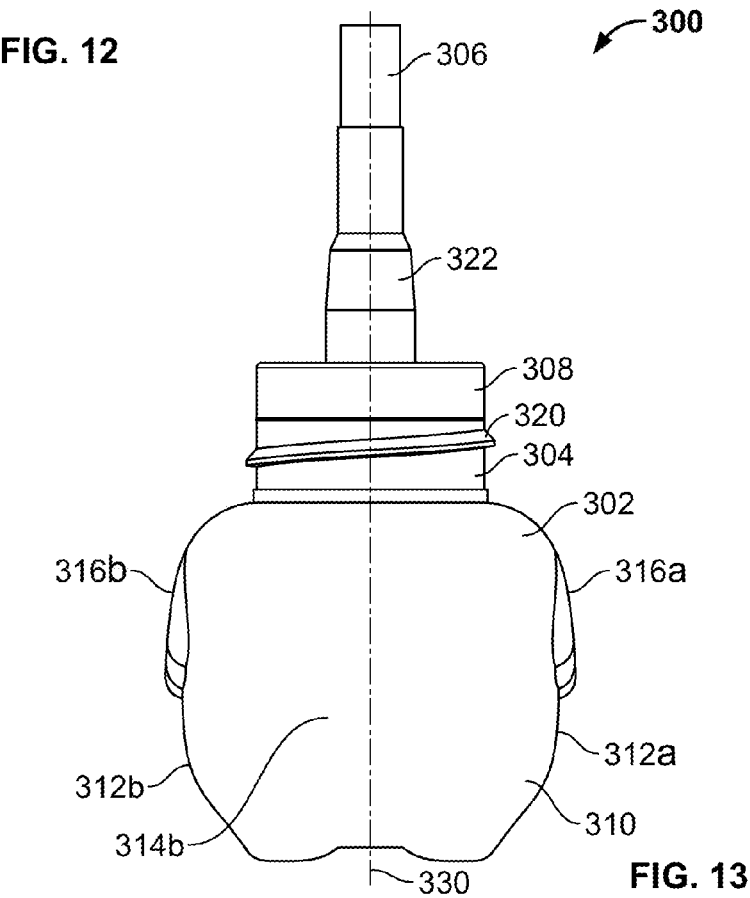
FIG. 13 is a side elevational view of the refill of FIG. 12.

A further refill 300 capable of insertion into the volatile material dispenser 20 is depicted in FIGS. 12 and 13. The refill 300 includes a container 302, a neck portion 304 extending upwardly from the container 302, a wick 306 in contact with a volatile material in the container 302 and extending out the neck portion 304, and a plug assembly 308 for holding the wick 306 within the neck portion 304. The container 302 includes a body 310 that is generally symmetrical about the neck portion 304 and includes opposing front and rear walls 312a, 312b and opposing side walls 314a, 314b. Shell-shaped protrusions 316a, 316b extend outwardly from the front and rear walls 312a, 312b, respectively. The protrusions 316a, 316b may alternatively have any other suitable shape. The neck portion 304 includes a thread 320 disposed on an outer surface thereof for attachment of a cap (not shown) thereto and the plug assembly 308 includes a sheath 322 extending upwardly therefrom, wherein the sheath 322 surrounds at least a portion of the wick 306.

Figure 14:
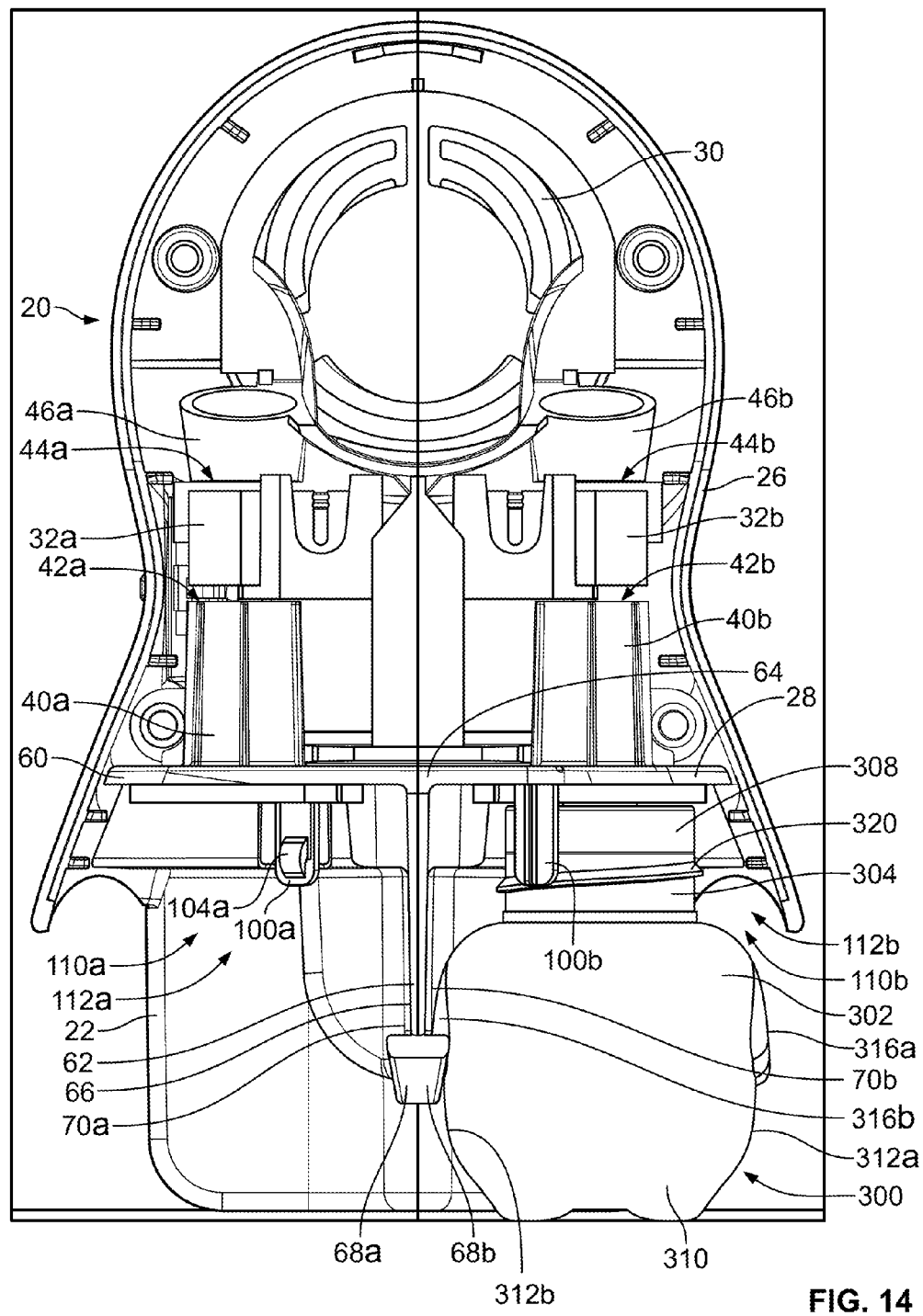
FIG. 14 is a front elevational view of the volatile material dispenser of FIG. 4 with the refill of FIGS. 12 and 13 inserted therein in a first orientation.

FIG. 14 depicts the refill 300 inserted into and retained within the second retention housing 112b of the dispenser 20 in a first orientation. Because the refill 300 is symmetrical about the neck portion 304 thereof, the refill 300 fits within the dispenser 20 in the same exact manner for the second orientation, so only the first orientation will be discussed herein. In the first orientation, the wick 306 and sheath 322 are inserted into the channel 42a and the refill 300 is pushed upwardly. During such movement, the stationary ribs 80b create an interference fit with the sheath 322 surrounding the wick 306 of the refill 300 (by way of a horizontal load being applied to the sheath 322), as discussed in detail above. The movable rib 82b allows for a bit of give or movement of the wick 306 and sheath 322 such that the interference fit is not too tight. In a retained position, wherein the stationary and movable ribs 80b, 82b partially retain the wick 306 and the sheath 322 in place, the protrusion 316a extending from the refill 300 sits on the ledge 68b to prevent downward movement of the refill 300. In the second orientation, which is rotated 180 degrees about a vertical axis 330 (FIG. 13) of the refill 300 from the first orientation, the protrusion 316b would prevent downward movement of the refill 300 in the same manner.

Although terms such as vertical, horizontal, downward, inward, etc. are utilized throughout the present application, such terms are not meant to limit the present invention, but instead, give relative direction when the dispenser 20 and/or refills 200, 300 are placed in a use position. Still further, although the dispensers 30 herein are described as having certain electrical features (LEDs, fan, heaters, etc.), the principles of the present invention may be utilized in dispensers having different electrical features.

Although multiple retention features are described herein, not all of such retention features are necessary for the present invention. Further, other refills having different shapes, sizes, and/or configurations may be utilized with the dispensers herein, so long as the appropriate retention features are present and capable of attachment with the dispensers.

Any of the embodiments described herein may be modified to include any of the structures or methodologies disclosed in connection with other embodiments.

INDUSTRIAL APPLICABILITY

The present invention provides volatile material dispensers that include multiple retention features to hold and retain one or more refills in different orientations. Specifically, the different retention features allow the refills to be inserted into and retained by the volatile material dispenser in one of two orientations.

Numerous modifications to the present disclosure will be apparent to those skilled in the art in view of the foregoing description. Accordingly, this description is to be construed as illustrative only and is presented to enable those skilled in the art to make and use the disclosure and to teach the best mode of carrying out same. The exclusive rights to all modifications that come within the scope of the appended claims are reserved.

I claim:

1. A method of attaching a refill to a volatile material dispenser, the method comprising the steps of:
providing a volatile material dispenser that includes a housing having first and second cavities disposed within the housing and each cavity adapted to accommodate a refill, each cavity includes a first implement formed within the cavity and which attaches a refill containing a volatile material to the housing by interacting with a neck portion of the refill, and a second implement formed within the cavity and which attaches the refill to the housing by interacting with a container portion of the refill;
inserting the refill into one of the first cavity or the second cavity and attaching the refill in a first orientation to the volatile material dispenser, wherein in the first orientation, the first implement and the second implement retain the refill; and
inserting the refill into one of the first cavity or the second cavity and attaching the refill in a second orientation to the volatile material dispenser, wherein in the second orientation, the first implement retains the refill.

2. The method of claim 1, wherein in the second orientation, the refill is oriented 180 degrees from an orientation of the refill in the first orientation.

3. The method of claim 2, wherein the first orientation of the refill inserted into the second cavity is oriented 180 degrees from the first orientation of the refill inserted into the first cavity.

4. The method of claim 3, wherein the first implement includes at least one of a plurality of stationary ribs, a movable rib, and a latch, wherein the plurality of stationary ribs and the movable rib create an interference with a sheath covering at least a portion of a wick that extends from the refill, and the latch that interacts with the neck portion of the refill, wherein the first implement attaches the refill to the housing by preventing downward movement of the refill.

5. The method of claim 4, wherein the second implement includes a ledge that interacts with a protrusion extending from the container portion of the refill to prevent downward movement of the refill.

* * * * *